United States Patent [19]

Distler

[11] 4,099,059
[45] Jul. 4, 1978

[54] TOMOGRAPHIC APPARATUS FOR PRODUCING TRANSVERSE LAYER IMAGES

[75] Inventor: Walter Distler, Erlangen, Germany

[73] Assignee: Siemens Aktiengesellschaft, Berlin & Munich, Germany

[21] Appl. No.: 776,767

[22] Filed: Mar. 11, 1977

[30] Foreign Application Priority Data

May 3, 1976 [DE] Fed. Rep. of Germany ....... 2619482

[51] Int. Cl.² .......................... A61B 6/00; G03B 41/16
[52] U.S. Cl. ................................ 250/445 T; 250/453; 269/323
[58] Field of Search .................. 250/445 T, 453, 491; 269/323

[56] References Cited

U.S. PATENT DOCUMENTS

| 3,974,388 | 8/1976 | Distler et al. ............... | 250/445 T |
| 3,983,399 | 9/1976 | Cox et al. .................... | 250/445 T |

Primary Examiner—Alfred E. Smith
Assistant Examiner—T. N. Grigsby
Attorney, Agent, or Firm—Hill, Gross, Simpson, Van Santen, Steadman, Chiara & Simpson

[57] ABSTRACT

The illustrated embodiment shows a patient supporting device for tomographic apparatus comprising two patient supports for cooperation in moving a patient through the apparatus by means of synchronously operated conveyors, the supports having a slight space therebetween to avoid interference with the scanning beam, and the confronting edges of the supports which provide the gap accommodating the scanning beam being shiftable as the housing is tilted in opposite longitudinal directions so that the gap is always in alignment with the plane of the scanning beam. Advantageously one patient support may be disengageable from the housing so as to be removable from the housing aperture and then vertically movable to a convenient level for receiving a patient.

5 Claims, 3 Drawing Figures

TOMOGRAPHIC APPARATUS FOR PRODUCING TRANSVERSE LAYER IMAGES

BACKGROUND OF THE INVENTION

The invention relates to a tomographic apparatus for producing transverse layer images of a radiographic subject, comprising a measuring arrangement comprising an x-ray source which produces an x-ray beam penetrating the radiographic subject, and whose cross-sectional extent perpendicular to the layer plane is equal to the layer thickness, and a radiation receiver which determines the intensity of radiation behind the subject, such apparatus further comprising a driving means for the measuring arrangement for producing rotational movements of the x-ray measuring arrangement, a measured value converter for transforming the signals supplied by the radiation receiver into a layer image, and a housing for the measuring arrangement which has an opening extending through it for receiving a patient supporting device with a patient.

For generating the layer image, the rotational movements can be effected in small equidistant angular amounts in alternating succession with linear displacements of the measuring arrangement along a straight line path perpendicular to the central ray of the x-ray beam, when a single radiation detector is used as the radiation receiver. However, it is also possible to omit the linear scanning movements if the radiation receiver is constructed of a plurality of radiation detectors whose signals are simultaneously processed by the measured value converter, and if the x-ray beam is of a fan-shaped configuration and strikes all the detectors simultaneously.

A tomographic apparatus of this type is known from U.S. Pat. No. 3,778,614. In the case of this known tomographic apparatus, a couch or support for the patient is present in the opening of the housing of the measuring arrangement and extends therethrough. As a result, the couch is also reproduced on the x-ray image.

SUMMARY OF THE INVENTION

The underlying task of the present invention is to construct a tomographic apparatus of the type initially cited in such a manner that the patient support is not shown in the x-ray image.

This task is solved according to the invention in that the patient supporting device consists of two couches or patient supports mounted on separate pedestals, each couch being secured to the housing by a holding device at one end, so that the surfaces of both couches lie in one plane, each couch being provided with a roll cloth type conveyor for moving the patient longitudinally. The two couches have a narrow gap therebetween within the housing opening, such gap having a width at least equal to the layer thickness of the tomographic layer to be generated. The examining x-ray beam thus passes through this narrow gap so that the patient supporting device is no longer detected.

A useful further development of the invention consists in that the housing is rotatably or swingably mounted about a horizontal axis lying transversely relative to the patient supporting device, and in that both patient supports are displaceable in their longitudinal directions in synchronism with the tilting movement of the housing. According to this further devlopment, the patient supporting device is not impinged by the beam energy even when the housing with the measuring arrangement is tilted for the purpose of selecting an angularly disposed body layer for examination, the gap between the two patient supports being adjusted according to the turning or swinging movement of the housing.

Other objects, features, and advantages of the present invention will be apparent from the following detailed description taken in connection with the accompanying sheets of drawings.

DESCRIPTION OF THE PREFERRED EMBODIMENT

Figure 1:
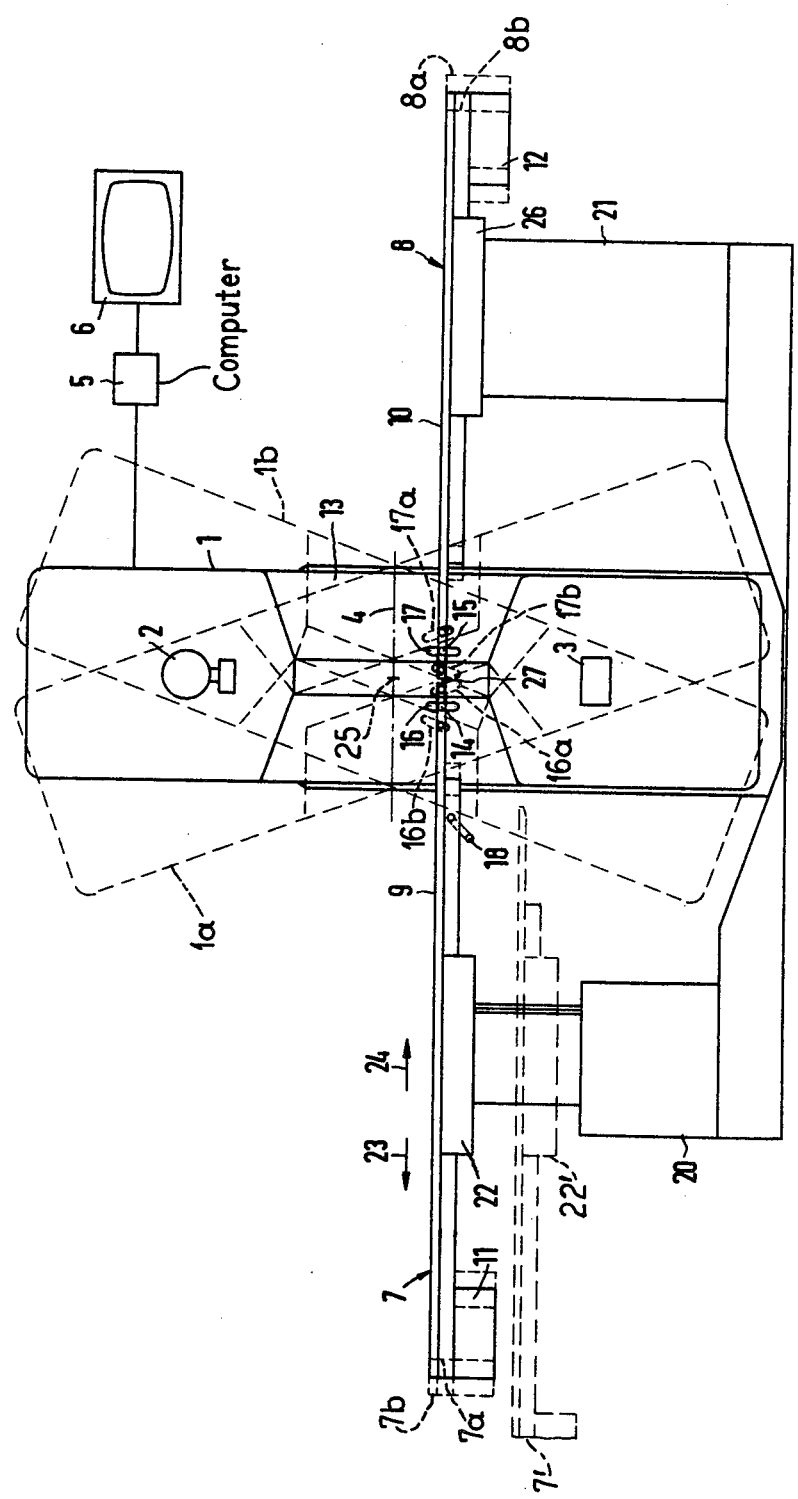
FIG. 1 is a somewhat diagrammatic side elevational view of a tomographic apparatus according to the present invention.

The tomographic apparatus represented by the drawings has a housing 1 in which a measuring arrangement is disposed comprising an x-ray tube 2 and a radiation receiver 3. The measuring equipment 2, 3 is rotatable about the axis 4 so as to provide for tomographic scanning of a transverse body layer in the known way. The radiation receiver 3 comprises a row of detectors which receive the fan-shaped x-ray beam of x-ray tube 2. The extent of the x-ray beam in the longitudinal direction of the patient is equal to the thickness of the layer to be examined, while the lateral extent of the x-ray beam corresponds, for example, to the transverse extent of the patient cross section within the apparatus. When the measuring arrangement 2, 3 is rotated, electric signals are supplied by the radiation receiver 3 from which a computer 5 calculates an image of the irradiated layer for reproduction on a viewing apparatus 6, for example.

Supporting the patient for an examination takes place on two patient supports or couches 7, 8, having surfaces lying in a common plane, and which are provided with respective roll cloth conveyors 9, 10, which can be driven by motors 11, 12. The drive of the conveyors 9, 10 is effected in synchronism, so that the patient can be moved from couch 7 to couch 8, for example, for the selection of the body layer to be scanned. The two ends of the couches 7, 8 lying in the housing opening 13, are secured by means of bolts 14, 15 to the housing 1, and more particularly the bolts 14, 15 engage in respective oblong slots 16 and 17 which run parallel to the central ray of the x-ray source 2. The bolts 14, 15 can be manually disengageable for the purpose of removing the couches 7, 8 from the housing opening 13. It is also sufficient if one couch only can be moved out of the opening 13, a lever 18 for actuation to withdraw the bolts 14 for this purpose being illustrated in FIG. 1. As best seen in FIG. 2, the lever 18 may be coupled with the bolts 14 by means of links 19 so that rotation of the lever 18, for example, will serve to retract the bolts 14 from the slots 16 against the action of a compression spring.

Figure 2:
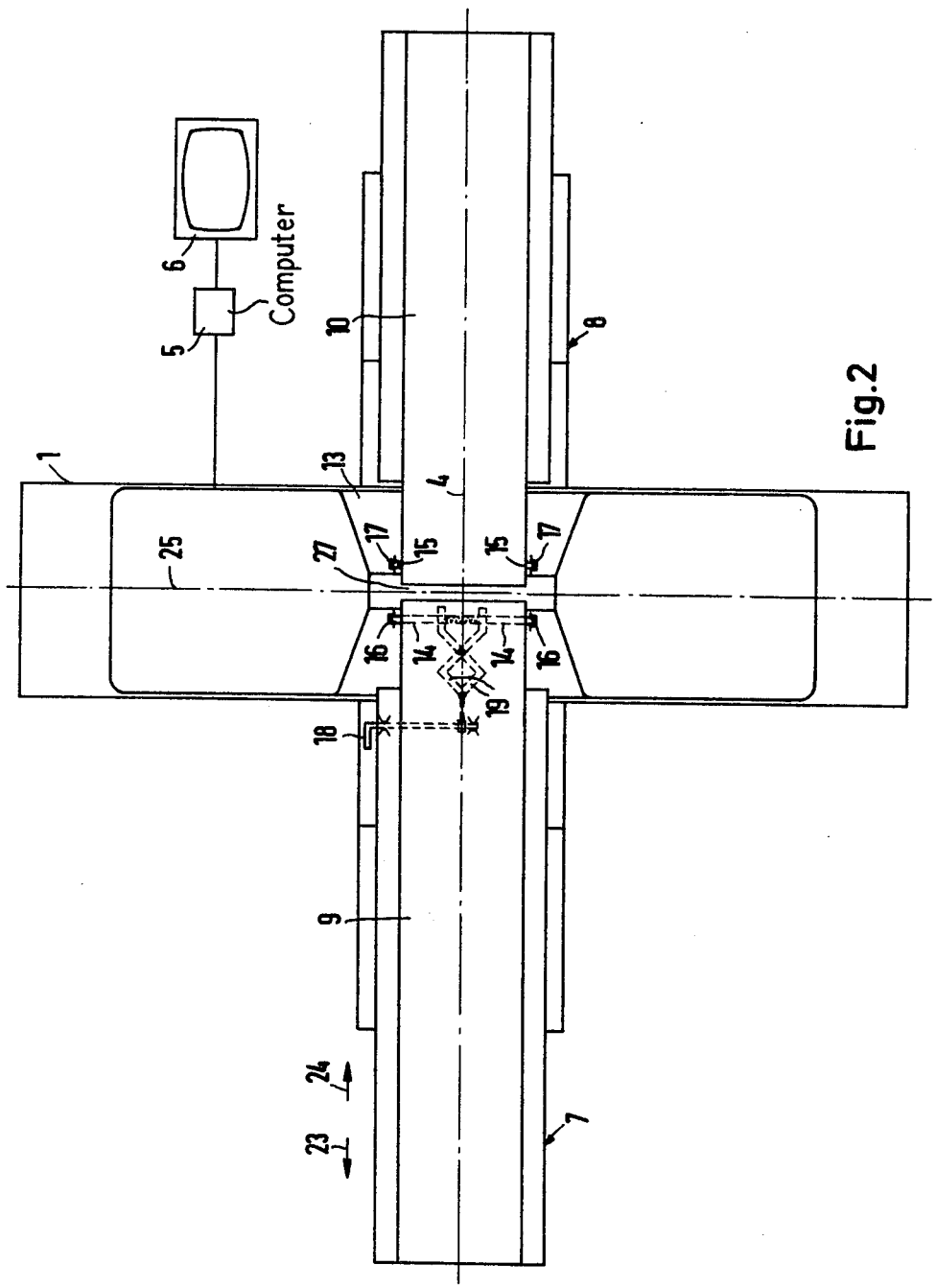
FIG. 2 is a diagrammatic top view of the apparatus of FIG. 1, the housing of FIG. 1 being shown in a sectional outline so as to reveal the details of the patient supporting device therein.

The couches 7 and 8 are mounted on respective pedestals 20 and 21, FIG. 1, and the couch 7 is shown as being retractable from the opening 13 and then movable in a vertical direction downwardly to a position such as indicated at 7'. The frame 22 is shown as being vertically movable relative to the pedestal 20 so as to assume a position as indicated at 22' as the couch 7 is lowered to a position such as 7'.

For positioning a patient, the bolts 14 are withdrawn from the oblong slots 16 by means of the lever 18 and the couch 7 is moved longitudinally by means of its supporting frame 22 in the direction of arrow 23 until its right end lies outside of the opening 13 of the housing 1. The couch 7 is then lowered into its position 7' indicated in dotted outline in FIG. 1. In this position, it is readily possible to position a patient on the couch, and in particular to transfer a patient to it from a hospital bed. The couch 7 is then raised again to its position on a level with the couch 8 and is displaced in the direction of arrow 24 until its right end again occupies the position shown by the solid lines in FIG. 1. The bolts 14 are then engaged in the oblong slots 16 so as to secure the couch 7 with the housing 1. The desired body layer to be examined can then be selected by switching on the conveyor cloths 9 and 10 and moving the patient in a longitudinal direction. In so doing, it is possible to move the patient from couch 7 to couch 8 with the roll cloths 9 and 10 moving at the same speed and in the same direction.

With the tomographic apparatus illustrated, it is possible to examine not only layers of the patient which lie at right angles to the patient couches 7 and 8, but also body layers which form an angle other than 90° in relation to the couches. For this purpose, the housing 1 with the measuring arrangement 2, 3 is rotatably or swingably mounted about a horizontal axis 25 (FIG. 2) which lies transversely relative to the patient supporting device 7, 8, and intersects the longitudinal axis 4, FIG. 1. In addition to the position indicated in solid lines in FIG. 1, the housing 1 with the measuring arrangement 2, 3 may therefore also assume, for example, the positions shown in dotted lines at 1a and 1b, in which a patient layer is examined which does not lie at right angles to the patient supporting device 7, 8.

The patient couch 8 is also longitudinally shiftable in relation to its mounting frame 26, so that when the housing 1 with the measuring arrangement 2, 3 is tilted to a position such as indicated at 1a, the patient couches 7, 8 are correspondingly shifted longitudinally to positions such as indicated in dash outline at 7a, 8a. Similarly, if the housing is tilted to a position such as indicated at 1b, the patient couches 7, 8 are shifted in the opposite longitudinal direction so as to assume positions such as indicated in dash outline at 7b, 8b. During such longitudinal shifting of the couches, the bolts 14, 15 are moved relatively in the oblong slots 16, 17, as the slots assume respective angled positions such as indicated at 16a, 17a, and 16b, 17b, respectively.

A small gap 27 is left free between the confronting ends of the couches 7 and 8 within the housing opening 13, such gap 27 having a width roughly equal to the thickness of the body layer to be examined by the measuring arrangement 2, 3. This gap 27 is also displaced when the housing 1 is tilted such that the beam emitted by the x-ray tube 1 and received by the radiation receiver 3 always passes through the gap 27 and is clear of the confronting edges of the couches 7 and 8. In this way, the patient positioning device 7, 8 is not reproduced on the layer image in any position of the housing 1 and the measuring arrangement 2, 3.

Figure 3:
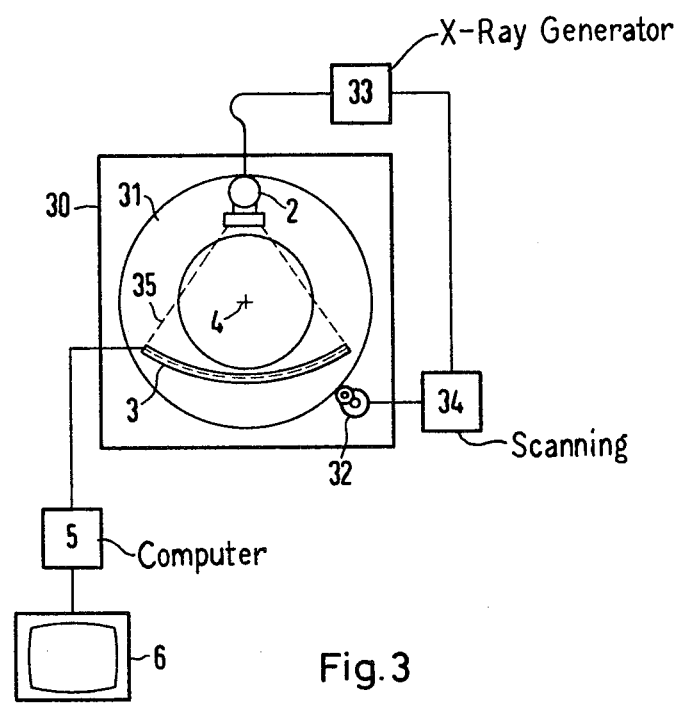
FIG. 3 is a diagrammatic view taken transversely along the axis 25 of FIG. 2 and indicating the internal construction of the tomographic apparatus and associated circuitry.

From FIG. 3 it will be apparent that a pivot mounting 31 in the form of a bearing ring for x-ray tube 2 and radiation receiver 3 is arranged in housing 1. Pivot mounting 31 is rotatably mounted about axis 4. The x-ray tube 2 and radiation receiver 3 are secured to the pivot mounting 31. The rotation of pivot mounting 31 about axis 4 is brought about by a drive system 32. Drive system 32 is energized during a scanning operation by means of a scanning control 34 which also serves to control energization of x-ray generator 33. By way of example, the scanning control 34 may cause drive system 32 and x-ray generator 33 to be simultaneously switched on for a scanning of the radiographic subject. Also by way of example, a rotation of measuring arrangement 2, 3 through an angle of 360° may take place during the scanning of the radiographic subject.

From FIG. 3, it is clearly apparent that the radiographic subject is substantially entirely permeated by the fan-shaped x-ray beam 35 of x-ray tube 2 within the examined body layer, in the illustrated embodiment. The longitudinal extent of the x-ray beam 35 may correspond to the longitudinal extent of gap 27 as a maximum.

Supplementary Disclosure

For the sake of a specific example, the patient supports 7 and 8 may resemble that illustrated in U.S. Pat. No. 3,974,388 issued Aug. 10, 1976 and assigned to the assignee herein. An arrangement for longitudinally and vertically moving a patient support arrangement is illustrated in U.S. Pat. No. 3,845,946 issued Nov. 5, 1974 and assigned to the assignee herein. Further details relating to the mounting of a patient support for longitudinal and vertical movement may be found in a pending application Ser. No. 661,514 filed Feb. 26, 1976 assigned to the assignee herein and identified by the assignee's reference VPA 75 P 5017, such pending U.S. application corresponding to German Application No. P 25 09 104.7 filed Mar. 3, 1975. It will be apparent to those skilled in the art how the patient support arrangement of U.S. Pat. No. 3,974,388 including the endless transport web or roll cloth and the drive motor may be bodily adjusted longitudinally and vertically from the referenced U.S. Pat. No. 3,845,946 and pending application.

With a longitudinal drive mechanism as shown in pending application Ser. No. 661,514, a suitable friction clutch may be interposed between the drive motor (18) and the chain pulls (19 and 20) allowing the force exerted by the walls of slots 16 and 17 during tilting of the housing 1 to exert an effective longitudinal shifting force on the respective bolts 14 and 15 for overcoming the frictional resistance of the friction clutches and effecting the desired longitudinal shifting the patient supports 7 and 8 along with the tilting movement of the housing 1, without energization of such drive motor (18).

It will be apparent that many modifications and variations may be effected without departing from the scope of the novel concepts and teachings of the present invention.

I claim as my invention:

1. Tomographic apparatus for producing transverse layer images of a radiographic subject, comprising an x-ray measuring arrangement including a radiation source which produces an x-ray beam penetrating the radiographic subject and having a predetermined extent perpendicular to the layer plane, and a radiation receiver which determines the intensity of radiation behind the subject during a scanning operation, a pivot mounting for the measuring arrangement accommodating rotational movements thereof during the scanning operation, and a housing for the measuring arrangement having an opening extending therethrough for receiving a patient supporting device with a patient, characterized by the patient supporting device comprising two individual patient supports for extending into the opening of the housing from opposite sides thereof, said supports having respective conveyors lying substantially in a common plane for moving the patient longitudinally and having a small gap therebetween with a width which is at least equal to the predetermined extent of the x-ray beam corresponding to the layer thickness to be examined.

2. Apparatus according to claim 1, characterized in that the housing is rotatably mounted relative to a horizontal axis lying transversely to the patient supporting device, the patient supports being longitudinally displaceable during swinging movement of the housing about such horizontal axis to maintain said gap in alignment with the x-ray beam.

3. Apparatus according to claim 2, characterized in that the two patient supports are coupled with the housing so as to be longitudinally shiftable in response to the swinging movement of the housing.

4. Apparatus according to claim 2 with said housing having oblong slots which extend generally parallel to the central ray of the x-ray source at each side of the x-ray beam, said patient supports having bolts engageable in said slots to couple the patient supports for longitudinal movement during swinging movement of the housing and such as to maintain the gap in alignment with the x-ray beam.

5. Apparatus according to claim 4, characterized in that at least one of said patient supports has manually actuatable means for disengaging the bolts from the slots of the housing to accommodate retraction of the support from the housing opening, said support being adjustable vertically to facilitate transfer of a patient thereto.

* * * * *